United States Patent
Kalbfeld et al.

(10) Patent No.: US 8,578,949 B2
(45) Date of Patent: Nov. 12, 2013

(54) MULTI-TEXTURE FLOSS AND METHODS OF MANUFACTURING MULTI-TEXTURE FLOSS

(75) Inventors: Russell G. Kalbfeld, Naperville, IL (US); David L. Barcus, Elmhurst, IL (US)

(73) Assignee: Sunstar Americas, Inc., Chicago, IL (US)

( * ) Notice: Subject to any disclaimer, the term of this patent is extended or adjusted under 35 U.S.C. 154(b) by 729 days.

(21) Appl. No.: 12/355,497

(22) Filed: Jan. 16, 2009

(65) Prior Publication Data
US 2009/0194134 A1 Aug. 6, 2009

Related U.S. Application Data

(60) Provisional application No. 61/024,955, filed on Jan. 31, 2008.

(51) Int. Cl.
*A61C 15/00* (2006.01)

(52) U.S. Cl.
USPC .......................................... 132/321; 132/325

(58) Field of Classification Search
USPC .......................................... 132/321, 326, 327
See application file for complete search history.

(56) References Cited

U.S. PATENT DOCUMENTS

| | | | |
|---|---|---|---|
| 3,747,611 A | 7/1973 | Bennington | |
| 3,837,351 A | 9/1974 | Thornton | |
| 3,896,824 A | 7/1975 | Thornton | |
| 4,008,727 A | 2/1977 | Thornton | |
| 4,052,994 A | 10/1977 | Thun | |
| 4,941,487 A | 7/1990 | VanBeneden | |
| 4,947,880 A * | 8/1990 | Tarrson et al. | 132/329 |
| 5,159,943 A | 11/1992 | Richards et al. | |
| 5,199,452 A | 4/1993 | Cheng | |
| 5,311,890 A | 5/1994 | Thornton | |
| 5,353,820 A | 10/1994 | Suhonen et al. | |
| 5,365,874 A | 11/1994 | Dorfman | |
| 5,433,226 A | 7/1995 | Burch | |
| 5,718,251 A | 2/1998 | Gray et al. | |
| 5,765,576 A | 6/1998 | Dolan et al. | |
| 5,842,489 A | 12/1998 | Suhonen et al. | |
| 7,213,604 B2 | 5/2007 | Romine | |
| 7,841,350 B2 | 11/2010 | Kernot | |

(Continued)

FOREIGN PATENT DOCUMENTS

| | | |
|---|---|---|
| CA | 2129422 | 1/1999 |
| WO | 2004/034922 | 4/2004 |

OTHER PUBLICATIONS

Office Action from the United States Patent and Trademark Office for U.S. Appl. No. 12/975,151 dated Oct. 12, 2012.

(Continued)

*Primary Examiner* — Rachel Steitz
(74) *Attorney, Agent, or Firm* — Michael Best & Friedrich LLP

(57) ABSTRACT

A multi-texture dental floss includes distinct and alternating segments having varying textures, including smooth segments and textured segments. The smooth segments are more easily inserted into the spaces between teeth, while the textured segments more effectively remove plaque and other debris therefrom. Methods of making the multi-texture floss are also disclosed, including methods that allow the floss to be made as a continuous thread having a plurality of alternating segments, such that the floss can be wound onto a spool for storage and dispensing.

13 Claims, 4 Drawing Sheets

(56) References Cited

U.S. PATENT DOCUMENTS

| | | |
|---|---|---|
| 2006/0225764 A1 | 10/2006 | Mark |
| 2006/0237028 A1* | 10/2006 | Hamidy ........................ 132/321 |
| 2011/0088717 A1 | 4/2011 | Kalbfelo et al. |

OTHER PUBLICATIONS

PCT/US2012/072076 International Search Report and Written Opinion dated Mar. 13, 2013 (11 pages).

Office Action from the U.S. Appl. No. 13/341,253 dated Jun. 3, 2013.

* cited by examiner

MULTI-TEXTURE FLOSS AND METHODS OF MANUFACTURING MULTI-TEXTURE FLOSS

CROSS REFERENCE TO RELATED APPLICATION

This application claims the benefit of and priority to U.S. Provisional Patent Application No. 61/024,955 filed Jan. 31, 2008. The entire contents of this application are hereby incorporated by reference.

BACKGROUND OF THE INVENTION

The present invention relates generally to dental floss, and more specifically to dental floss comprising segments having different textures.

Advancements in materials and manufacturing techniques have resulted in a wide range of options when it comes to dental floss. For example, until fairly recently, dental floss options consisted primarily of waxed or unwaxed floss available in various flavors. Currently however, a wide variety of flosses are available, with each variety having its own benefits and limitations. Examples of different materials from which dental floss is currently made include nylon, Polytetrafluoroethylene (PTFE) or "Teflon®," ultra-high molecular weight polyethylene (UHMWPE), and polyester, among others.

Another dental floss option relates to the texture of the floss. Some flosses, such as those formed of PTFE, are designed to be relatively thin and smooth, which allows them to more easily pass through the space between adjacent teeth. Other flosses are designed to be relatively thick, textured, or coarse to remove plaque and other debris more effectively from the larger spaces between adjacent teeth. While many people appreciate the ease of use associated with a relatively thin and smooth floss, many dentists recommend the thick and coarse floss for more effective cleaning.

SUMMARY

In some embodiments, the invention provides a dental treatment device in the form of a thread or floss, the thread including a plurality of first segments and a plurality of second segments. Each first segment extends a first length and includes a first texture and a first cross-sectional dimension. Each second segment extends between adjacent ones of the first segments for a second length, and include a second texture and a second cross-sectional dimension. The second texture is substantially dissimilar from the first texture, and the second cross-sectional dimension is substantially dissimilar from the first cross-sectional dimension. The thread includes alternating ones of the first and second segments.

In other embodiments, the invention provides a method of making dental floss that includes applying tension to a length of thread to thereby reduce at least one cross-sectional dimension of the length of thread. A portion of the tensioned length of thread is bonded, the tension is released from the length of thread such that the bonded portion of the length of thread maintains the reduced cross-sectional dimension.

In still other embodiments, the invention provides a method of making multi-texture dental floss that includes unwinding a length of thread from a feed spool and feeding the length of thread through first feed rollers. The length of thread is fed from the first feed rollers to first tensioning rollers, and wound about a drum to apply tension to the length of thread. Applying tension to the length of thread reduces at least one cross sectional dimension of the length of thread. A portion of the tensioned length of thread is bonded by applying an adhesive, which is allowed at least partially to cure while the thread is wound upon the drum. The tension is released from the length of thread by unwinding the thread from the drum to second tensioning rollers, and the length of thread is fed from the second tensioning rollers to second feed rollers. The length of thread is also wound onto a take-up spool.

Figure 1:
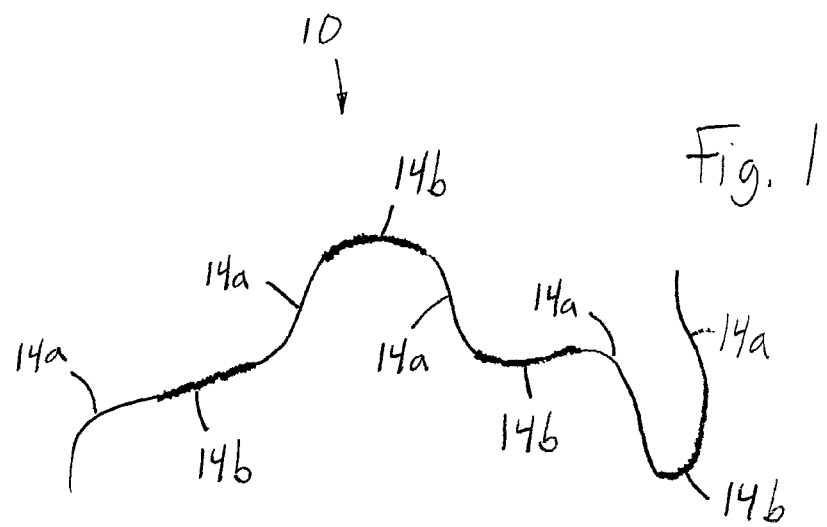
FIG. 1 illustrates a length of multi-texture dental floss embodying the invention.

Before at least one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways.

DETAILED DESCRIPTION

FIG. 1 illustrates a length of multi-texture dental floss 10 embodying the invention. The floss 10 is comprised of alternating segments of floss 14a and 14b having different textures. In the illustrated embodiment, the segments 14a are relatively smooth, while the segments 14b are textured. The segments 14a are configured to more easily fit into the spaces between teeth, while the segments 14b are configured to more effectively remove plaque and debris from the spaces between teeth. The length of floss 10 illustrated in FIG. 1 represents only a portion of a larger length of floss that may be wound onto a spool for storage and dispensing, as discussed further below.

Figure 2:
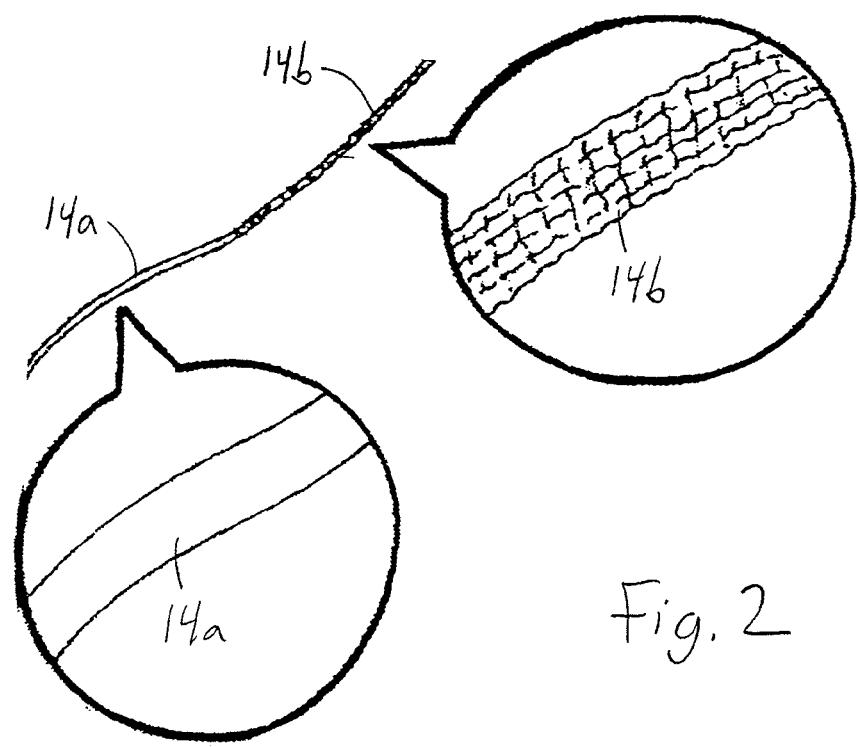
FIG. 2 is an enlarged view of portions of the multi-texture dental floss of FIG. 1.

With reference also to FIG. 2, in some embodiments, the segments 14a may have a thickness in at least one direction that is less than a thickness of the textured segments 14b. For example, the segment 14a may have a thickness in at least one direction of approximately 0.5 mm or less, while the segment 14b may have a thickness in at least one direction of approximately 1 mm or more. In some instances, the segment 14a will have a thickness less than the segment 14b in only one direction. For example, the segment 14a may be formed substantially as a ribbon, having one relatively small cross-sectional dimension, and another relatively large cross-sectional dimension. In such cases, the larger cross-sectional dimension may be substantially equal to a cross-sectional dimension of the segment 14b.

The segment 14b may also be formed substantially as a ribbon but will generally include a minimum cross-sectional dimension that is larger than the minimum cross-sectional dimension of the segment 14a. Furthermore, while the segment 14a is generally provided with a smooth surface texture to ease manipulation of the floss into the space between teeth, the segment 14b is generally provided with a textured surface to more effectively remove plaque and other debris from the space between the teeth. The textured surface may be a result of tightly weaving floss fibers in a way that provides peaks and valleys within the floss, or may be the result of a relatively loose weave that provides a generally circular cross section defined by relatively soft and compliant fibers. The segment 14a may also be fabricated in a manner that results in the segment 14a being more stiff than the segment 14b. In this regard, the end of a segment 14a can be used to thread a length of floss 10 "end first" into an interdental space, rather than manipulating a central portion of the floss upwardly or downwardly into the space between adjacent teeth. This feature may be particularly helpful for individuals with dental appliances or braces because it allows the floss to be inserted between the dental appliance or braces and the gum line.

Figure 3:
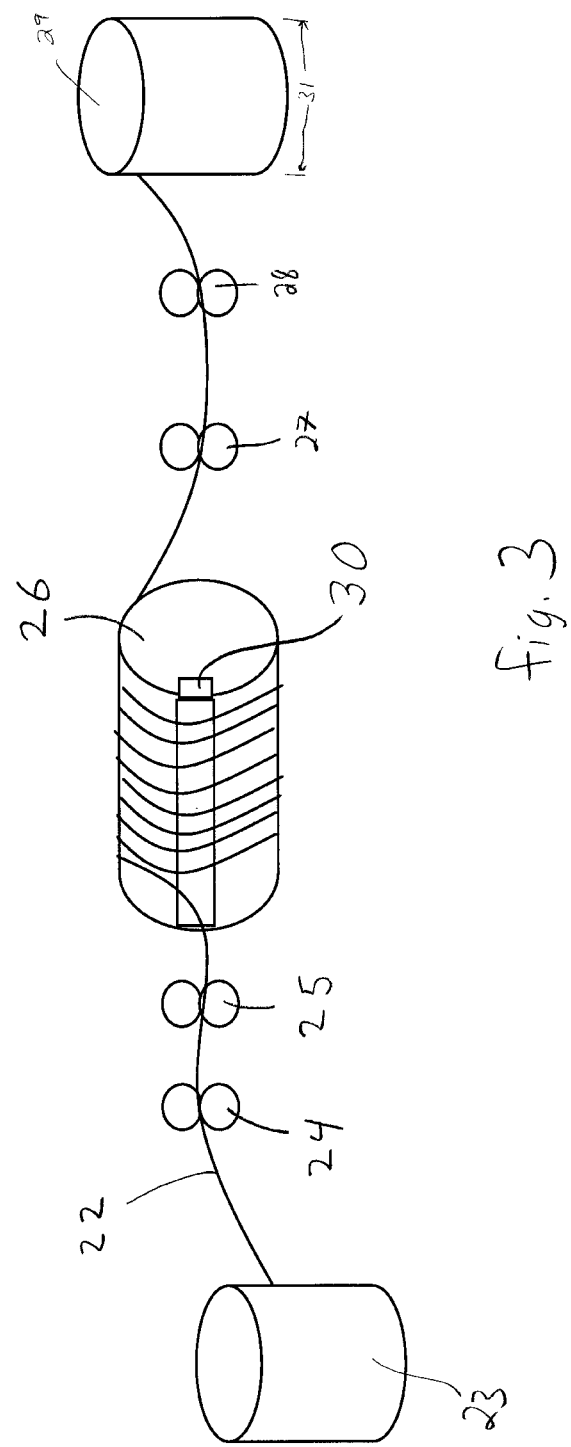
FIG. 3 is a schematic view of a method for manufacturing the multi-texture dental floss of FIG. 1.

FIG. 3 schematically illustrates a first method for making the above-described multi-texture floss 10. The method includes applying tension to a length of floss 22 and winding the taught length of floss 22 around a drum 26. Applying tension to the floss 22 reduces the cross-sectional area and corresponding cross-sectional dimensions of the floss 22. The tension also draws individual floss fibers more closely together, thereby smoothing peaks and valleys that may be present in, for example, a woven floss.

More specifically, the method utilizes a feed spool 23 wound with a supply of uncoated or otherwise untreated floss fiber. The length of floss 22 is uncoiled from the feed spool 23 by a pair of feed rollers 24. The feed rollers 24 then position the floss 22 to be received by first tensioning rollers 25. The first tensioning rollers 25 are preferably rotated by a driving device (e.g. motor, not shown) and direct the length of floss 22 onto the drum 26. The speed of the first tensioning rollers 25 is adjusted so that the length of floss 22 is pulled taught and brought under tension as it is wound onto the drum 26.

The drum 26 is selected to have a circumference that is substantially equal to the desired length of floss that will include at least one smooth segment 14a and at least one textured segment 14b of the finished multi-texture floss 10. After a suitable length of taught floss 22 has been wound around the drum, an adhesive is applied to a section 30 of the drum 26 and thus to the floss 22 by rolling, spraying, or otherwise applying the adhesive in an axial direction from one end of the drum 26 to the other. One example of a suitable adhesive includes cyanoacrylate, however other adhesives may also be used. In some embodiments, the adhesive is applied to the drum 26 and floss 22 in an approximately one to two inch wide strip. In the illustrated construction, the section 30 includes an axially-extending channel into which the adhesive may be sprayed. By spraying the adhesive into a channel the adhesive can be applied uniformly about the exposed outer surfaces of the length of floss 22.

After the adhesive has set, the floss 22 is unwound from the drum 26. The floss 22 then passes through second tension rollers 27. The second tension rollers 27 are preferably rotated by a driving device (e.g., motor, not shown) at an adjustable speed to maintain the tension in the floss 22. After passing through the second tension rollers 27, the tension that was previously applied to the floss to reduce its cross-sectional area is relieved and the sections of floss that did not receive adhesive return to their original size, shape, tension, and texture. These sections become the textured sections 14b of the finished multi-texture floss 10. However, the portions of the floss 22 to which the adhesive was applied maintain the reduced cross-sectional area, greater tension than the original tension and reduced cross-sectional dimensions provided by applying tension to the floss, and the surface of the floss is more uniform than before processing as a result of the bonding and smoothing properties provided by the adhesive. These portions become the smooth segment 14a of the finished multi-texture floss 10. The floss 22 then passes through a feed rollers 28 that position the floss 22 for coiling on a take-up spool 29. The take-up spool 29 is generally cylindrical and includes an outer diameter 31. The outer diameter 31 is selected to be relatively large so that as the floss 22 continues to cure, it takes on a more linear configuration.

In some embodiments, as the finished floss 10 is unwound from the take-up spool 29, it may be coated under light tension on standard coating equipment in a second manufacturing operation. Such coatings may include paraffin wax, minapause, flavoring, or coloring. In yet other embodiments, the finished floss 10 may be packaged into spools, such as the spools discussed below, or may be cut to length and packaged as individual strands having at least one each of a smooth segment 14a and a textured segment 14b. In yet another embodiment, the floss may undergo the light tension coating procedure before being wound onto the take-up spool 29 as an additional step of the multi-texturing process.

It should be appreciated that instead of applying a single strip of adhesive to the floss 22 wound upon the drum 26, multiple strips of adhesive could also be applied, resulting in multiple smooth and textured segments 14a, 14b for each individual winding of floss 22. In this regard, the circumference of the drum 26 and the number of adhesive applications may be selected to meet the demands of a particular manufacturing process.

Figure 4:
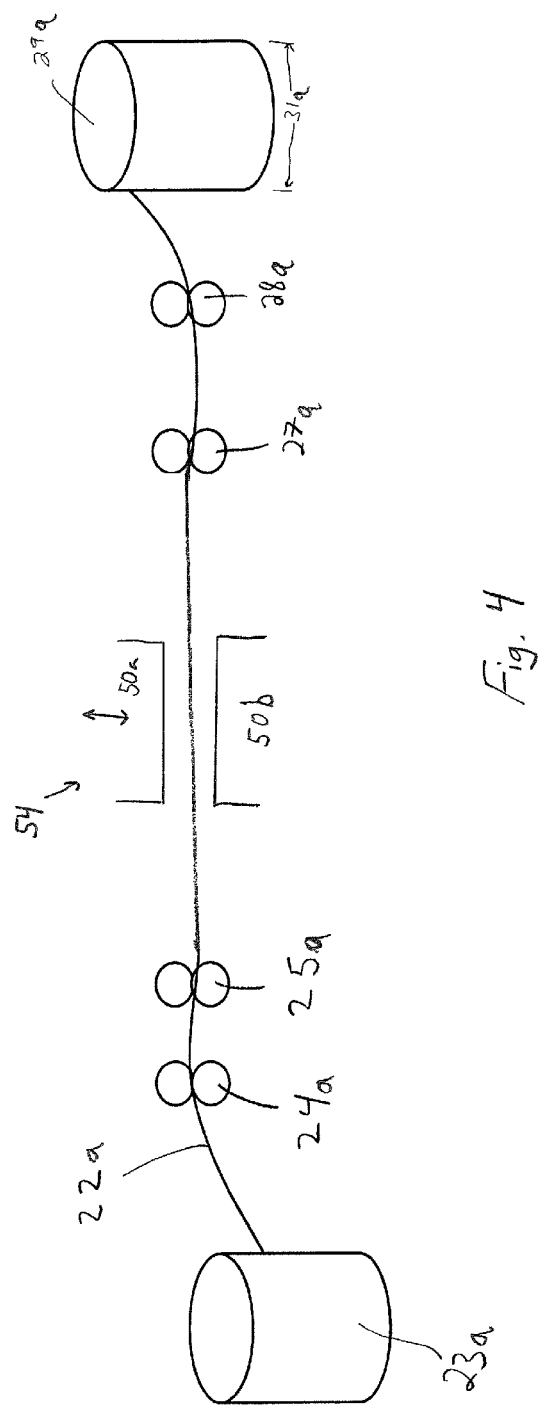
FIG. 4 is a schematic view of an alternate method of manufacturing the multi-texture dental floss of FIG. 1.

FIG. 4 illustrates another method for making the above-described multi-texture floss 10 including the use of sonic welding. In this method, a length 22a of uncoated or otherwise untreated floss is unwound from a feed spool 23a. The floss is then fed through first feed rollers 24a and first tension rollers 25a similar to the uncoiling and feeding steps described above. In the embodiment of FIG. 4, the first tension rollers 25a cooperate with second tension rollers 27a such that the floss extending between the first and second tension rollers 25a, 27a is under tension, thereby reducing its cross-sectional area and cross-sectional dimensions as described above. The tensioned length of floss 22a is advanced between first and second dies 50a, b of a sonic welding device 54. The first and second dies 50a, b are closed and the portion of the floss between the dies is sonically welded. The sonic welding bonds the floss fibers together such that, once tension on the floss is removed by advancing the floss past the second tension rollers 27a, the sonically welded portion of floss maintains its reduced cross-sectional area and reduced cross-sectional dimensions. The sonically welded portion of floss thereafter form a smooth segment 14a of the finished multi-texture floss 10, and the untreated portions of floss on either side of the sonically welded portion of floss become textured segments 14b of the finished multi-texture floss 10. The length of the smooth segment 14a will substantially correspond to the size of the dies 50a, b. In some embodiments, the smooth segments 14a have a length of between about one and two inches.

After forming one smooth segment 14a, the length of floss is advanced to position a new portion of floss between the dies of the sonic welding device. The length of the textured segments 14b can be adjusted by advancing the floss by varying amounts through the rollers 25a, 27a between welding operations. As with the method described above, the floss 22 passes through a pair of feed rollers 28a that position the floss 22a for coiling on a take-up spool 29a. The take-up spool 29a is generally cylindrical and includes an outer diameter 31a. The floss 22a may similarly be coated under light tension on standard coating equipment in a second manufacturing operation. Such coatings may include paraffin wax, minapause, flavoring, and/or coloring. In yet other embodiments, the finished floss 10 may be packaged into spools, such as the spools discussed below, or may be cut to length and packaged as individual strands having at least one each of a smooth segment 14a and a textured segment 14b. In yet another embodiment, the floss may undergo the light tension coating procedure before being wound onto the take-up spool 29a as an additional step of the multi-texturing process.

Examples of known flosses that may be manufactured using the methods described above to create the multi-textured floss 10 include GUM® brand Butler Weave® floss, GUM® brand Expanding Floss, GUM® brand Eez-Thru® floss, and GUM® brand waxed or unwaxed flosses. These and other suitable flosses may be made from one or more materials such as nylon, polytetrafluoroethylene (PTFE), ultrahigh molecular weight polyethylene (UHMWPE), and polyester, among others.

For example, GUM® brand Butler Weave® floss is a braided nylon dental floss of approximately 840 denier that may be waxed or unwaxed. GUM® brand Expanding Floss is a twisted waxed nylon dental floss of approximately 700 denier that, when untreated, expands when abraded or upon contact with moisture during use. When treated to create multi-texture floss 32 using one of the methods described above, only the textured segment 40 of the Expanding Floss will expand during use. GUM® brand Eez-Thru® floss is a monofilament of polytetrafluoroethylene (PTFE) of between about 810 and 990 denier. GUM® brand waxed or unwaxed flosses are formed of twisted, shred resistant fine nylon of approximately 700 denier.

Figure 5:
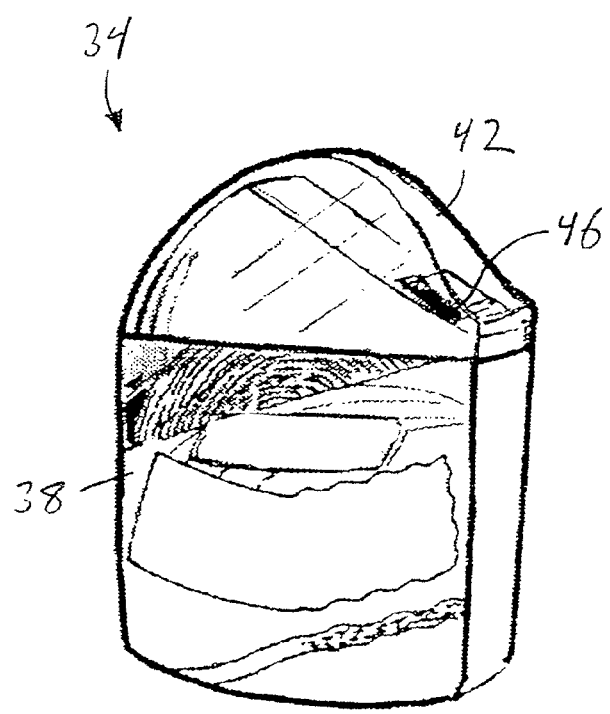
FIG. 5 is a perspective view of a dispenser for the multi-texture dental floss of FIG. 1.

FIG. 5 illustrates a dispenser 34 for the multi-texture floss 10. While various configurations are possible, the illustrated dispenser 34 includes a body 38 and a cover 42. The body 38 rotatably supports a spool (not shown) upon which a length of floss 10 having a plurality of segments 14a, 14b is wound. Because the smooth segments 14a tend to retain the shape of the spool onto which they are wound, the spool preferably has a diameter that is greater than the diameter of traditional dental floss spools. In this way, the curvature of the smooth segments 14a once removed from the spool is reduced.

The body 38 also defines an opening 46 through which the floss 10 can be dispensed. The opening 46 may include, among other things, a reduced aperture, a flap portion biased against the floss, or a detent arrangement to provide a tactilely detectable indexing of the floss as the alternating smooth segments 14a and textured segments 14b are withdrawn from the body 38 and pass through the opening 46. Floss cutting and floss retention tabs (not shown) may also be provided on the body 38, or the floss may be severed and retained by structure provided on the cover 42 when the cover 42 is closed against the body 38.

The invention claimed is:

1. A dental treatment device comprising:
   a thread including:
      a plurality of first segments, each first segment extending a first length and including a first texture, a first tension, and a first cross-sectional dimension; and
      a plurality of second segments, each second segment extending between adjacent ones of the first segments for a second length, the second segments including a second texture, a second tension, and a second cross-sectional dimension, the second texture substantially dissimilar from the first texture, the second tension greater than the first tension, and the second cross-sectional dimension smaller than the first cross-sectional dimension, wherein the second segments are stiffer than the first segments, and wherein the thread includes alternating ones of the first and second segments.

2. The dental treatment device of claim 1, wherein the thread includes a substantially rectangular cross section, and wherein the first and second cross-sectional dimensions are the height of the rectangular cross section.

3. The dental treatment device of claim 1, further comprising a spool rotatably carried by a housing, and wherein the thread is wound about the spool for storage and dispensing.

4. The dental treatment device of claim 1, wherein the thread is formed from a plurality of fibers.

5. The dental treatment device of claim 4, wherein the plurality of fibers of the second segments are bonded to one another.

6. The dental treatment device of claim 5, wherein the plurality of fibers of the second segments are bonded with an adhesive.

7. A dental treatment device comprising:
   a length of thread formed from a plurality of fibers, said fibers having the same material composition throughout the length of the thread, the thread including:
      a plurality of first segments, each first segment extending a first length and including a first texture and a first cross-sectional dimension, each first segment having its plurality of fibers in a first weave under a first tension; and
      a plurality of second segments, each second segment extending between adjacent ones of the first segments for a second length and composed of fibers continuous with the fibers of the adjacent first segments, the second segments including a second texture and a second cross-sectional dimension, the second texture substantially dissimilar from the first texture and the second cross-sectional dimension substantially dissimilar from the first cross-sectional dimension, each second segment having its plurality of fibers in a second weave under a second tension that is tighter than the first tension.

8. The dental treatment device of claim 7, wherein the plurality of fibers of the second segments are bonded to one another.

9. The dental treatment device of claim 7, wherein the second cross-sectional dimension is less than the first cross-sectional dimension.

10. The dental treatment device of claim 7, wherein the second segments are stiffer than the first segments.

11. A dental treatment device formed from a continuous single thread comprising:
   a plurality of first segments, each first segment having a first tension and a first texture; and
   a plurality of second segments, each second segment having a second tension greater than the first tension and a second texture substantially dissimilar from the first texture,
   wherein the first and second segments are integrally formed in the thread and alternate with each other.

12. The dental treatment device of claim 11, wherein the thread is composed of a plurality of fibers, and wherein the fibers of the second segment are bonded.

13. The dental treatment device of claim 12, wherein the fibers of the second segments are bonded with an adhesive.

* * * * *